United States Patent
Nomura et al.

(10) Patent No.: US 9,889,186 B2
(45) Date of Patent: Feb. 13, 2018

(54) ORAL VACCINE HAVING IMPROVED CELLULAR IMMUNITY INDUCTION POTENCY

(71) Applicants: ANGES MG, INC., Osaka (JP); BIOLEADERS CORPORATION, Daejeon (KR)

(72) Inventors: Takashi Nomura, Osaka (JP); Akiko Temma, Osaka (JP); Takahiro Nakazawa, Osaka (JP); Ryuichi Morishita, Osaka (JP); Il-Han Lee, Daejeon (KR)

(73) Assignees: MORISHITA JINTAN CO., LTD., Osaka (JP); BIOLEADERS CORPORATION, Daejeon (KR)

( * ) Notice: Subject to any disclaimer, the term of this patent is extended or adjusted under 35 U.S.C. 154(b) by 0 days.

(21) Appl. No.: 14/785,364

(22) PCT Filed: Apr. 18, 2014

(86) PCT No.: PCT/JP2014/061099
§ 371 (c)(1),
(2) Date: Oct. 19, 2015

(87) PCT Pub. No.: WO2014/171546
PCT Pub. Date: Oct. 23, 2014

(65) Prior Publication Data
US 2016/0089429 A1    Mar. 31, 2016

(30) Foreign Application Priority Data
Apr. 19, 2013 (JP) .................. 2013-088800

(51) Int. Cl.
| | |
|---|---|
| A61K 35/74 | (2015.01) |
| A61K 39/07 | (2006.01) |
| A61K 39/12 | (2006.01) |
| A61K 35/747 | (2015.01) |
| A61K 9/14 | (2006.01) |
| C12N 7/00 | (2006.01) |
| A61K 39/00 | (2006.01) |

(52) U.S. Cl.
CPC ............ *A61K 39/12* (2013.01); *A61K 9/14* (2013.01); *A61K 35/747* (2013.01); *C12N 7/00* (2013.01); *A61K 2039/521* (2013.01); *A61K 2039/523* (2013.01); *A61K 2039/54* (2013.01); *A61K 2039/542* (2013.01); *C12N 2710/20034* (2013.01)

(58) Field of Classification Search
None
See application file for complete search history.

(56) References Cited

PUBLICATIONS

Maria Chávarri (Immunology and Microbiology >> "Probiotics", book/ Chapter 23: Encapsulation Technology to Protect Probiotic Bacteria. pp. 501-540. Published: Oct. 3, 2012. https://www.intechopen.com/download/pdf/39599).*
International Search Report dated Jul. 15, 2014 in International Application No. PCT/JP2014/061099.
International Preliminary Report on Patentability dated Oct. 20, 2015 in International Application No.PCT/JP2014/061099.
Lowy, D.R. et al., "Genital human papillomavirus infection" Proc. Natl. Acad. Sci. USA, Mar. 29, 1994; 91(7):2436-40.
Pisani, P. et al., "Estimates of the worldwide mortality from eighteen major cancers in 1985. Implications for prevention and projections of future burden". Int. J. Cancer. Dec. 2, 1993; 55(6):891-903.
Gao, L. et al., "Immune response to human papillomavirus type 16 E6 gene in a live vaccina vector". J Gen Virol. Jan. 1994; 75 (Pt 1):157-64.
Meneguzzi G., et al., "Immunization against human papillomarvirus type 16 tumor cells with recombinant vaccinia viruses expressing E6 and E7". Virology. Mar. 1991;181(1)62-9.
Hallez S. et al., "Pre-clinical immunogenicity and anti-tumour efficacy of a deleted recombinant human papillomarvirus type 16 E7 protein". Anticancer Res. Jul.-Aug. 2004; 24(4):2265-75.
Tabata Y., Ikada Y., "Phagocytosis of polymer microspheres by macrophages" Adv Polym Sci. 1990; 94:107-141.
Sewaki T., "Generation of mucosal vaccine utilizing lactobacillus display system", Yakugaku Zasshi, Nov. 2009; 129(11):1327-32.
Hasegawa H., New Food Industry, 2008, vol. 50, pp. 1-8.
Inno Y., "Production of living lactic acid bacterium in powder by the pulse shock wave dryer system", Osaka-fu Kankyo Norin Suisan Sogo Kenkyusho Kenkyu Hokoku, 2009, No. 2, pp. 21-23.
Kei Kawana, "Development of HPV therapeutic vaccine" Medical Tribune, Nov. 3, 2011 (vol. 44 No. 44) p. 46 (with English translation).
Supplemental European Search Report dated Nov. 30, 2016 in corresponding European Application No. 14785570.

(Continued)

*Primary Examiner* — Jennifer Graser
(74) *Attorney, Agent, or Firm* — Wenderoth, Lind & Ponack, L.L.P.

(57) ABSTRACT

An oral preparation for the prophylaxis or treatment of a disease with infection by a pathogen, containing a killed lactic acid bacterium expressing, on the surface, an antigen of the pathogen, or a microparticulated form thereof, which has an average particle size of 2.68-30 μm. An oral preparation for inducing cellular immunity to a target antigen, containing a killed lactic acid bacterium expressing the target antigen on the surface or a microparticulated form thereof, which has a particle size of 2.68-30 μm.

16 Claims, 6 Drawing Sheets

(56) References Cited

PUBLICATIONS

Her et al., "Preparation of probiotic powder by the spray freeze-drying method", Journal of Food Engineering, 150: 70-74, Nov. 4, 2014.

Rieux et al., "Transport of nanoparticles across an in vitro model of the human intestinal follicle associated epithelium", European Journal of Pharmaceutical Sciences, 25(4-5): 455-465, Jul. 1, 2005.

* cited by examiner

FIG. 1
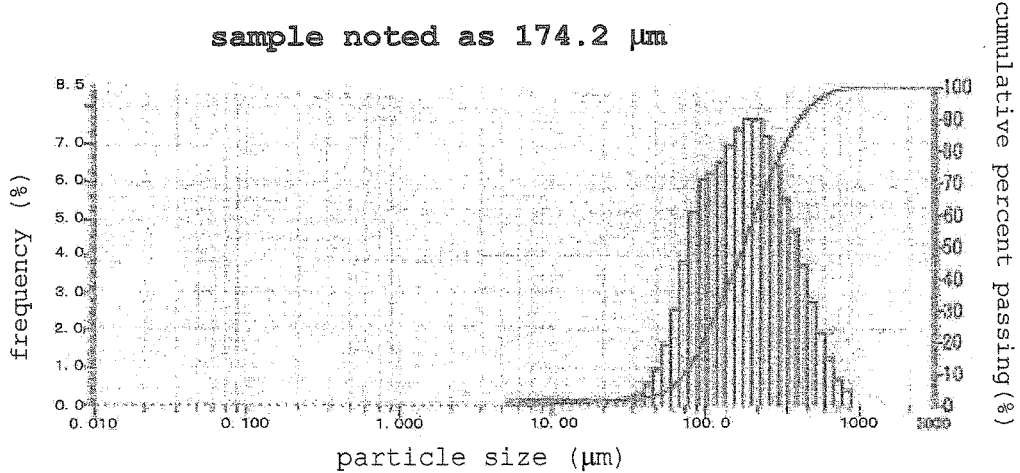
| median size | 174.2 um | 10 um or below | 0.6% |
| minimum particle size | 5.8 um | 5.8 um or below | 0.1% |
| maximum particle size | 890.1 um | | |
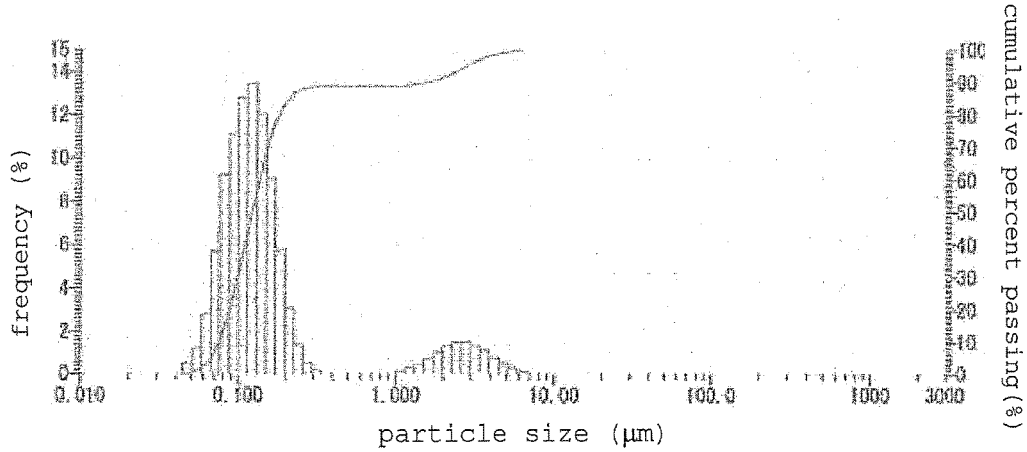
| median size | 0.12 um | 1 um or below | 88.8% |
| minimum particle size | 0.05 um | 0.5 um or below | 88.8% |
| maximum particle size | 6.72 um | 0.3 um or below | 88.6% |

FIG. 6

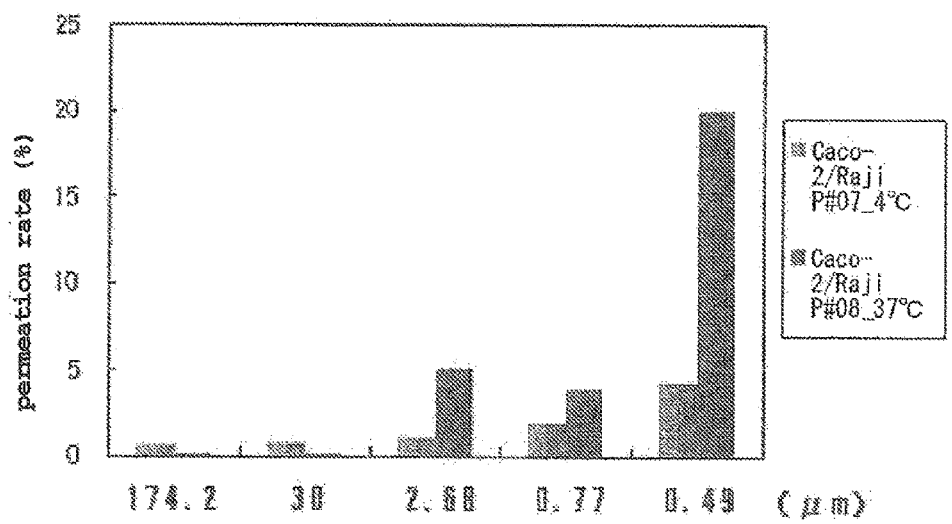

FIG. 7

| No. | | particle size (μm) | dispersing medium | dose | n |
|---|---|---|---|---|---|
| 1 | - | - | saline | - | 10 |
| 2 | lactic acid bacterium | 174.2 | saline | 1 mg/mouse | 10 |
| 3 | lactic acid bacterium | 30 | saline | 1 mg/mouse | 10 |
| 4 | lactic acid bacterium | 2.68 | saline | 1 mg/mouse | 10 |
| 5 | lactic acid bacterium | 0.77 | saline | 1 mg/mouse | 10 |
| 6 | lactic acid bacterium | 0.49 | saline | 1 mg/mouse | 10 |
| 7 | lactic acid bacterium | 0.49 | saline | 0.3 mg/mouse | 10 |
| 8 | lactic acid bacterium | 0.49 | saline | 0.1 mg/mouse | 10 |
| 9 | lactic acid bacterium | 0.49 | saline | 0.03 mg/mouse | 10 |

ORAL VACCINE HAVING IMPROVED CELLULAR IMMUNITY INDUCTION POTENCY

TECHNICAL FIELD

The present invention relates to an oral preparation for the prophylaxis or treatment of diseases with infection by pathogens. The present invention also relates to an oral preparation for inducing cellular immunity against a target antigen.

BACKGROUND ART

It is assumed that not less than 50% of adults are infected with human papillomavirus (HPV) in the world and, among papillomaviruses, particularly four types of HPV 16, 18, 31 and 45 have been confirmed to cause not less than 80% of cervical cancer (non-patent document 1).

All over the world, cervical cancer is a cancer that highly frequently occurs in women next to breast cancer and, according to the World Health Organization, not less than 500,000 cervical cancer patients are produced every year worldwide and not less than 300,000 people are assumed to die of cervical cancer every year. Particularly in developing countries and less developed countries, it is the main cause of death of women (non-patent document 2). According to the IARC statistics, it is reported that a method most effective for eradicating HPV infection for a long term in developing countries particularly where the number of chronically infected people is extremely high as compared to advanced countries is administration of HPV preventive vaccines.

Methods for vaccine development relating to cervical cancer largely focus on two: prophylactic vaccine and therapeutic vaccine. Prophylactic vaccine aims to prevent a host from being infected with HPV by a strong neutralizing antibody produced by HPV L1/L2 antigen protein. On the other hand, therapeutic vaccine targeting HPV E6/E7 aims to induce specific cellular immunity to prevent progression of disease when infection with HPV has been confirmed, or cause regression of lesion already formed and malignant tumor.

Since E6/E7 protein of HPV is a cancer specific antigen involved in canceration of cells infected with HPV and the like, therapeutic vaccine utilizing E6/E7 protein as a target of cervical cancer immunotherapy has been studied. In fact, reports have documented that administration of HPV E6/E7 protein synthesized by a microorganism system to a rat injected with tumor cells inhibited or delayed tumor formation (non-patent documents 3, 4 and 5).

In consideration of the fact that people infected with HPV are mainly concentrated in less developed countries, the development of a method of producing a vaccine to HPV economically and stably is strongly demanded for the prophylaxis and treatment of cervical cancer caused by papillomavirus.

The present inventors developed a therapeutic vaccine for cervical cancer containing a killed lactic acid bacterium expressing E7 protein of HPV on the surface as an active ingredient. This therapeutic vaccine is orally administered to cause uptake of the E7 protein into patients via the intestine and induce specific cellular immunity to the E7 protein in the cervix, thereby preventing patients infected with HPV (e.g., patients having cervical cancer precancerous lesion CIN3) from shift to cervical cancer. The vaccine shows superior safety and effectiveness in clinical tests (non-patent document 6).

At present, in an undergoing exploratory clinical test, the production cost of a preparation of a killed lactic acid bacterium expressing E7 protein of HPV, which is the active ingredient of the oral therapeutic vaccine, on the surface is comparatively expensive. If efficacy equivalent to the effectiveness at present can be shown even by reducing the dose from that in the exploratory clinical test (four 250 mg capsules, once per day), the cost of the preparation becomes lower, practicalization of the therapeutic drug becomes higher, and an economical burden on patients can be reduced.

On the contrary, uptake of orally ingested fine particles into the body via the intestine is regulated by mesentery M cell permeability of the fine particles. It is known that particles having a size exceeding 10 μm show markedly low phagocytosis by M cell (non-patent document 7).

DOCUMENT LIST

Non-Patent Documents non-patent document 1: Lowy, D. R. et al., Proc. Nat. Acad. Sci., 91:2436, 1994
non-patent document 2: Pisani, P. et al., Int. J. Cancer, 55:891, 1993
non-patent document 3: Gao, L. et al., J. Gen. Viol., 75:157, 1994
non-patent document 4: Meneguzzi, G. et al., Virology, 81:62, 1991
non-patent document 5: Sophie H. et al., Anticancer Res, July 2004; 24: 2265-2276
non-patent document 6: Kei Kawana, Medical Tribune, Nov. 3, 2011 (VOL. 44 NO. 44) p. 46
non-patent document 7: Tabata Y, Ikada Y. Adv Polym Sci 94:107-141, 1990

SUMMARY OF THE INVENTION

Problems to be Solved by the Invention

In view of the above-mentioned situation, the present invention aims to provide a formulation technique for reducing an effective dose of an oral therapeutic vaccine containing, as an active ingredient, a killed lactic acid bacterium expressing a target antigen on the surface.

Means of Solving the Problems

The present inventors considered that once the mesentery M cell permeability can be improved by reducing the particle size of killed lactic acid bacterium that expresses target antigen on the surface by disrupting same, the absorption efficiency into the body increases, along with which antigen specific cellular immunity induction potency increases, and the effective amount of a therapeutic vaccine by oral administration can be reduced. As expected, mesentery M cell permeability increased more as the killed lactic acid bacterium was pulverized to a smaller particle size, and the amount of the target antigen that permeates mesentery M cell increased, which was confirmed using in vitro M cell model. The antigen specific cellular immunity induction potency by oral administration was improved by disrupting a killed lactic acid bacterium having a particle size of 174.2 μm, which is a drug substance, to a particle size of 30 μm or 2.68 μm. Unexpectedly, however, when the killed lactic acid bacterium was microparticulated to a size below 2.68 μm, mesentery M cell permeability improved in the in vitro model but antigen specific cellular immunity induction potency conversely decreased. Further studies were conducted based on these findings, which resulted in the completion of the present invention.

Accordingly, the present invention relates to the following.

[1] An oral preparation for the prophylaxis or treatment of a disease with infection by a pathogen, comprising a killed lactic acid bacterium expressing, on the surface, an antigen of the pathogen, or a microparticulated form thereof, which has an average particle size of 2.68-30 μm.
[2] The oral preparation of [1], wherein the pathogen is an intracellular infectious pathogen.
[3] The oral preparation of [2], wherein the intracellular infectious pathogen is a virus.
[4] The oral preparation of [3], wherein the virus is human papilloma virus.
[5] The oral preparation of [1], wherein the antigen of the pathogen is an internal antigen of the pathogen.
[6] The oral preparation of [5], wherein the antigen of the pathogen is E7.
[7] The oral preparation of [1] for the prophylaxis or treatment of the disease with infection by the pathogen by inducing cellular immunity to the antigen of the pathogen.
[8] An oral preparation for inducing cellular immunity to a target antigen, comprising a killed lactic acid bacterium expressing the target antigen on the surface or a microparticulated form thereof, which has an average particle size of 2.68-30 μm.
[9] The oral preparation of [8], wherein the target antigen is an antigen of a pathogen.
[10] The oral preparation of [9], wherein the pathogen is an intracellular infectious pathogen.
[11] The oral preparation of [10], wherein the intracellular infectious pathogen is a virus.
[12] The oral preparation of [11], wherein the virus is human papilloma virus.
[13] The oral preparation of [9], wherein the antigen of the pathogen is an internal antigen of the pathogen.
[14] The oral preparation of [9], wherein the antigen of the pathogen is E7.
[15] A killed lactic acid bacterium expressing a target antigen on the surface or a microparticulated form thereof, which has an average particle size of 2.68-30 μm, for use in the prophylaxis or treatment of a disease with infection by a pathogen by oral administration.
[16] The killed lactic acid bacterium or a microparticulated form thereof of [15], wherein the pathogen is an intracellular infectious pathogen.
[17] The killed lactic acid bacterium or a microparticulated form thereof of [16], wherein the intracellular infectious pathogen is a virus.
[18] The killed lactic acid bacterium or a microparticulated form thereof of [17], wherein the virus is human papilloma virus.
[19] The killed lactic acid bacterium or a microparticulated form thereof of [15], wherein the antigen of the pathogen is an internal antigen of the pathogen.
[20] The killed lactic acid bacterium or a microparticulated form thereof of [19], wherein the antigen of the pathogen is E7.
[21] The killed lactic acid bacterium or a microparticulated form thereof of [15], wherein the disease with infection by the pathogen is prevented or treated by inducing cellular immunity to the antigen of the pathogen.
[22] A method for the prophylaxis or treatment of a disease with infection by a pathogen, comprising orally administering an effective amount of a killed lactic acid bacterium expressing, on the surface, an antigen of the pathogen, or a microparticulated form thereof, which has an average particle size of 2.68-30 μm, to a patient.
[23] The method of [22], wherein the pathogen is an intracellular infectious pathogen.
[24] The method of [23], wherein the intracellular infectious pathogen is a virus.
[25] The method of [24], wherein the virus is human papilloma virus.
[26] The method of [22], wherein the antigen of the pathogen is an internal antigen of the pathogen.
[27] The method of [26], wherein the antigen of the pathogen is E7.
[28] The method of [22] for the prophylaxis or treatment of the disease with infection by the pathogen by inducing cellular immunity to the antigen of the pathogen.

Effect of the Invention

According to the present invention, cellular immunity induction potency to a target antigen in oral administration can be improved by setting the average particle size of a killed lactic acid bacterium expressing the target antigen on the surface or a microparticulated form thereof to fall within the range of 2.68-30 μm, and therefore, the effective dose of an oral vaccine containing the killed lactic acid bacterium as an active ingredient can be reduced.

BRIEF DESCRIPTION OF THE DRAWINGS

FIG. 1 shows particle size distribution of a killed lactic acid bacterium in a non-microparticulated preparation (average particle size 174.2 μm) and a microparticulated preparation (particle size 0.12 μm).
FIG. 6 shows the results of in vitro M cell permeability of a killed lactic acid bacterium or a microparticulated form thereof having various particle sizes. The left bar shows permeability at 4° C. and the right bar shows permeability at 37° C.
FIG. 7 shows group constitution and test schedule of an in vivo immunity induction potency comparison test.

DESCRIPTION OF EMBODIMENTS

Figure 2:
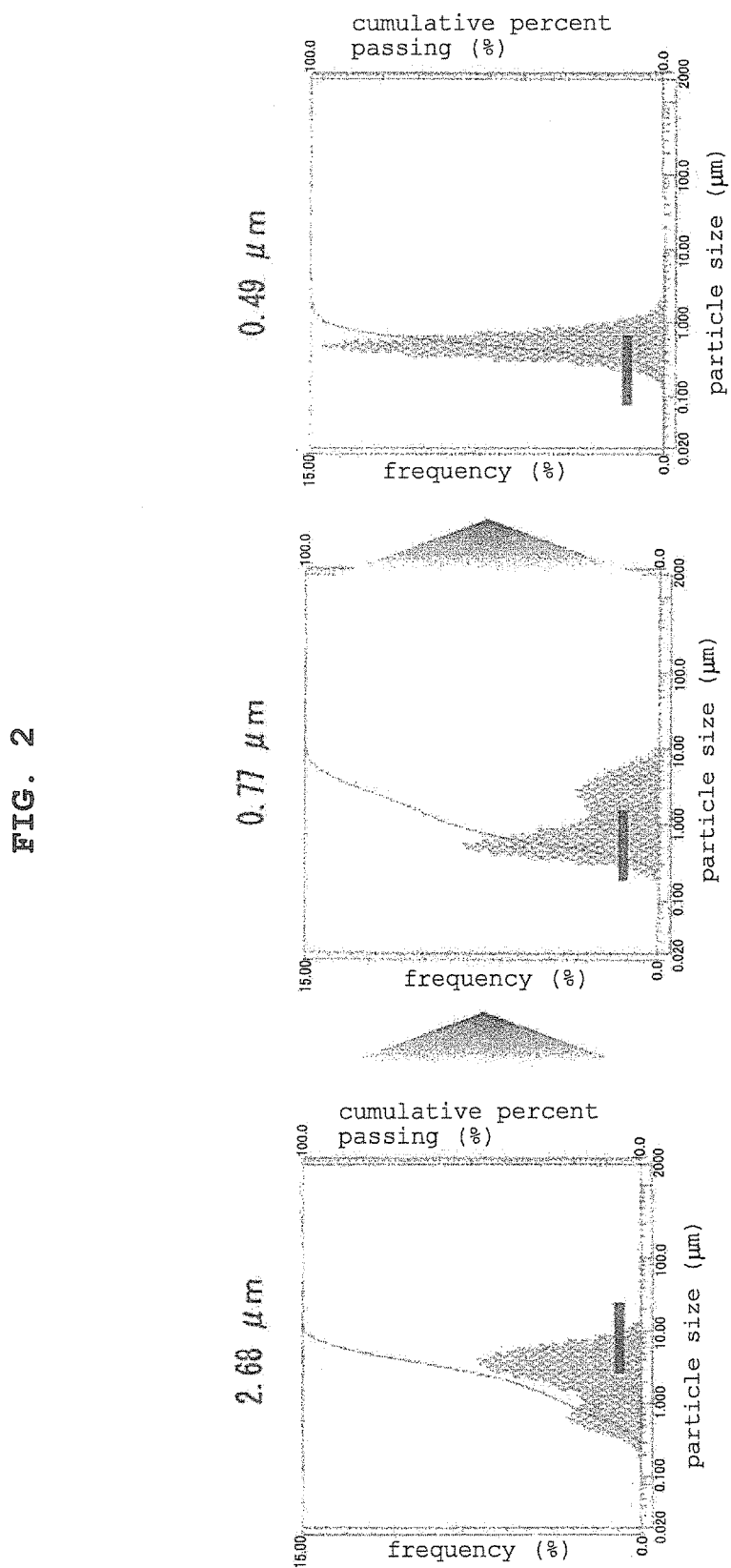
FIG. 2 shows particle size distribution of a killed lactic acid bacterium in microparticulated preparations (particle size 2.68 μm, 0.77 μm, 0.49 μm).

The present invention provides an oral preparation containing a killed lactic acid bacterium expressing a target antigen on the surface or a microparticulated form thereof, which has an average particle size of 2.68-30 µm. The oral preparation of the present invention can be used for inducing cellular immunity to the target antigen. Using an antigen of a pathogen as a target antigen, the oral preparation of the present invention can be used for the prophylaxis or treatment of diseases with infection by the pathogen.

The target antigen is not particularly limited as long as it is recognized as a foreign substance by the immune system of an administration subject (e.g., human) of the oral preparation of the present invention, and induces an acquired immune reaction, and any substance can be used. Examples of the substance include, but are not limited to, polypeptide (including peptide, protein), glycolipid, sugar, nucleic acid and the like. Since the oral preparation of the present invention is superior in the activity to induce cellular immunity, an antigen which is uptaken into antigen presenting cells, processed, presented on MHC class I, and recognized by T cell receptor (TCR) expressed on cytotoxic T cells (CD8 T cells) is preferably used. In general, cytotoxic T cell recognizes polypeptide and glycolipid presented on MHC class I via TCR. Therefore, the target antigen to be used in the present invention is preferably a peptide or glycolipid that can be, when presented on MHC class I of an administration subject (e.g., human), recognized by TCR on cytotoxic T cell of the administration subject (e.g., human); protein, pathogen, cell, or a part (extract etc.) of pathogen or cell, which is degraded by proteasome in the cell of an administration subject (e.g., human) to produce such peptide or glycolipid, or the like. More preferably, the target antigen to be used in the present invention is a peptide that can be, when presented on MHC class I of an administration subject (e.g., human), recognized by TCR on cytotoxic T cell of the administration subject (e.g., human); or a protein which is degraded by proteasome in the cell of an administration subject (e.g., human) to produce such peptide.

The kind of the target antigen includes antigen of a pathogen, tumor antigen, food antigen, allergen and the like, and is not particularly limited. In one embodiment, the target antigen is an antigen of a pathogen. Using antigen of a pathogen as the target antigen, cellular immunity to the antigen of the pathogen can be efficiently induced and a disease with infection by the pathogen can be prevented or treated. Examples of the pathogen include, but are not particularly limited to, bacteria, virus, parasitic worm, fungus and the like that cause extracellular or intracellular infections.

Since the oral preparation of the present invention is superior in the activity to induce cellular immunity, and it is known that intracellular infectious pathogens and cancer are eliminated from the body by cellular immunity, preferably an antigen of intracellular infectious pathogen and an antigen related to cancerated cells (tumor antigen, for example, protein containing mutation due to canceration), more preferably an antigen of intracellular infectious pathogen, is used as the target antigen. In infectious diseases caused by intracellular infectious pathogens, cellular immunity is mainly induced, and cells infected with the intracellular infectious pathogens and presenting the antigen of the pathogen on MHC class I are killed by cytotoxic T cells, whereby the intracellular infectious pathogens are eliminated ex vivo. Therefore, using an antigen of intracellular infectious pathogen as an antigen to be used for the oral preparation of the present invention, the cellular immunity to the antigen is efficiently induced, and elimination of the cells infected with the intracellular infectious pathogens by the induced cellular immunity is promoted, and disease with infection by the intracellular infectious pathogen can be prevented or treated.

Examples of the intracellular infectious pathogen include, but are not particularly limited to, virus; intracellular parasitic bacteria such as *Rickettsia*, Chlamydiae, *Phytoplasma*, *Mycoplasma* and the like; intracellular parasitic protozoa such as *Toxoplasma, Leishmania, Malaria plasmodium, Schistosomiasis, Phytomyxea* and the like, and the like, preferably virus.

Examples of the virus include, but are not particularly limited to, human papillomavirus (HPV), HTLV-1, EBV, HCV, HBV, influenza virus, polio virus, Japanese encephalitis virus, measles virus, mumps virus, rubella virus, rabies virus, yellow fever virus, varicella virus, HAV, dengue virus, rotavirus, parvovirus, HIV and the like. In one embodiment, the virus is oncogenic virus such as HPV, HTLV-1, EBV, HCV, HBV and the like. In one embodiment, the virus is HPV.

In the present invention, when an antigen of a pathogen is used as a target antigen, an internal antigen and a surface antigen of the pathogen can be used as the antigen of the pathogen. The oral preparation of the present invention is superior in the activity to induce cellular immunity, even when an internal antigen inaccessible by induction of humoral immunity alone is used as an antigen of a pathogen, cellular immunity to the internal antigen is induced, and cells presenting the internal antigen are killed by cytotoxic T cells, whereby the pathogen is eliminated from the body and a disease with infection by the pathogen can be prevented or treated.

In one embodiment, in the oral preparation of the present invention, HPV antigen is used as the target antigen. Examples of the HPV antigen include E1, E2, E4, E5, E6, E7, L1, L2 and the like. Among these HPV antigens, E1, E2, E4, E5, E6 and E7 correspond to the internal antigens. Among the aforementioned HPV antigens, E6 and E7 are superior in the therapeutic effect of cellular immunity induction for HPV infectious diseases.

In the present invention, the disease with infection by a pathogen encompasses infection with pathogen, diseases and symptoms caused by the infection. For example, in the case of HPV, HPV infectious disease encompasses HPV infection; precancerous lesion (cervix intraepithelial tumor (CIN)) caused by HPV infection, cervical cancer, a part of cancers of anus, vulvar and vaginal cancer, penile cancer, oropharyngeal cancer, condyloma acuminatum and the like.

The lactic acid bacterium to be used in the oral preparation of the present invention encompasses genus *Lactobacillus*, genus *Streptococcus*, genus *Lactococcus*, genus *Enterococcus* and genus *Bifidobacterium*. Representative examples of the genus *Lactobacillus* include *Lactobacillus acidophilus* (*L. acidophilus*), *Lactobacillus casei* (*L. casei*), *Lactobacillus plantarum* (*L. plantarum*), *Lactobacillus fermentum* (*L. ferementum*), *Lactobacillus delbrueckii* (*L. delbrueckii*), *Lactobacillus johnsonii* (*L. johnsonii* LJI), *Lactobacillus reuteri* (*L. reuteri*), *Lactobacillus gasseri* (*L. gasseri*), *Lactobacillus mali* (*L. mali*), *Lactobacillus buchneri* (*L. buchneri*), *Lactobacillus gallinarum* (*L. gallinarum*), *Lactobacillus amylovorus* (*L. amylovorus*), *Lactobacillus brevis* (*L. brevis*), *Lactobacillus rhamnosus* (*L. rhamnosus*), *Lactobacillus kefir* (*L. kefir*), *Lactobacillus paracasei* (*L. paracasei*), *Lactobacillus crispatus* (*L. crispatus*), *Lactobacillus bulgaricus* (*L. bulgaricus*) and the like. Representative examples of the genus *Streptococcus* include *Streptococcus thermophilus* (*S. thermophilus*), *Streptococcus gordonii* (*S. gordonii*) and the like. Representative examples of the genus *Lactococcus* include *Lactococcus lactis* (*L. lactis*), *Lactococcus cremoris* (*L. cremoris*) and the like. Representative examples of the genus *Enterococcus* include *Enterococcus faecalis* (*E. faecalis*), *Enterococcus faecium* (*E. faecium*) and the like. Representative examples of the genus *Bifidobacterium* include *Bifidobacterium infantis* (*B. infantis*), *Bifidobacterium bifidum* (*B. bifidum*), *Bifidobacterium longum* (*B. longum*), *Bifidobacterium pseudolongum* (*B. psuedolongum*), *Bifidobacterium breve* (*B. breve*), *Bifidobacterium lactis* Bb-12 (*B. lactis* Bb-12), *Bifidobacterium catenulatum* (*B. catenulatum*) and *Bifidobacterium adolescentis* (*B. adolescentis*) and the like. More preferably, genus *Lactobacillus* is used.

In the oral preparation of the present invention, the target antigen is expressed on the surface of lactic acid bacterium. A technique for expressing the target antigen on the surface of microorganisms such as lactic acid bacteria and the like is called cell surface display technique, and widely known to those of ordinary skill in the art. In general, a surface protein of microorganisms such as bacteria, yeast and the like is used as a surface anchoring motif, and the target antigen, which is a foreign protein, is expressed on the surface of the microorganism. That is, a lactic acid bacterium is transformed with an expression vector that expresses a fusion protein wherein a surface anchoring motif and a target antigen are linked, whereby a lactic acid bacterium expressing the target antigen on the surface can be obtained. Surface anchoring motif is largely divided into extracellular membrane protein, lipoprotein, secretory protein, and surface organ protein such as flagellar protein. Examples of a surface anchoring motif preferable for surface expression by lactic acid bacteria include genes of poly-γ glutamic acid synthetic complex derived from the genus *Bacillus* strain (pgsB, pgsC, pgsA, pgsBCA, preferably pgsA) (WO 03/014360) and the like. As for a method of expressing a target antigen on the surface of microorganisms such as lactic acid bacteria and the like, refer to WO 2004/035795, WO 2004/108937, WO 2005/075653, WO 2008/115019, WO 2010/079982, WO 2010/079991, JP-A-2007-131610 and the like.

A lactic acid bacterium expressing the target antigen on the surface can be cultured under known conditions or conditions analogous thereto. For example, a lactic acid bacterium is generally cultured in a liquid medium containing glucose, yeast extract, peptone and the like at about 25-45° C. for about 4-72 hr aerobically or anaerobically, and bacterial cells are harvested from the culture medium and washed to give wet bacterial cells of a lactic acid bacterium expressing the target antigen on the surface.

The oral preparation of the present invention uses a killed bacterium of a lactic acid bacterium expressing the target antigen on the surface. The technique for killing lactic acid bacteria is well known in the pertinent technical field, and is not particularly limited as long as it impairs survivability of the lactic acid bacteria. Examples of the method for killing lactic acid bacteria include eradication by a treatment of lactic acid bacteria with a chemical substance such as ether, formalin, chlorine, mercury, alcohol, β-propiolactone and the like, exposure to heat, ultrasonic waves, UV, X-ray and the like, and the like. Killing of lactic acid bacteria is preferably performed in such a manner lactic acid bacteria lose survivability whereas loss of antigenicity of the target antigen expressed on the surface of the lactic acid bacteria is minimized, and the plasmid used for transformation is removed. From such aspect, lactic acid bacteria are preferably killed by a heat treatment. JP-B-4902845 discloses a production method of a superior preparation of a killed lactic acid bacterium, comprising adding a surfactant and carbonate to the basic medium for the lactic acid bacterium, culturing the bacterium while maintaining pH of the culture medium to 6.0-7.0 during culture, killing the culture by a heat treatment to remove living bacteria present in the culture medium, remove recombinant gene-containing plasmid present in the cells of transformed lactic acid bacterium, and strengthen the immunity function.

The oral preparation of the present invention is characterized in that the average particle size of a killed lactic acid bacterium or a microparticulated form thereof expressing the target antigen, which is the active ingredient thereof, on the surface is set to 2.68-30 μm. Setting the average particle size to fall within the range of 2.68-30 μm, an orally-administered killed lactic acid bacterium expressing the target antigen on the surface or a microparticulated form thereof can strongly induce cellular immunity to the target antigen.

Since lactic acid bacterium is generally a rod-shaped bacterium having a long diameter of about 7 μm, the average particle size of a microparticulated form of a killed lactic acid bacterium is generally below 7 μm. In one embodiment, the average particle size of a microparticulated form of a killed lactic acid bacterium expressing the target antigen on the surface, which is contained in the oral preparation of the present invention, is not less than 2.68 μm and less than 7 μm.

In the present specification, the average particle size of a killed lactic acid bacterium or a microparticulated form thereof is the median size (d50) of a volume standard particle size distribution obtained by measuring the particle size of a dry preparation of the killed lactic acid bacterium or a microparticulated form thereof by a laser diffraction scattering method, and can be measured using, for example, LA-920, LA-950V2 (both types manufactured by HORIBA). When the particle size cannot be measured by a laser diffraction scattering method from the properties, the particle size may be measured from the images of SEM (scanning electron microscope). When it can be measured by the both methods, the measurement results by a laser diffraction scattering method is preferentially employed.

In the present specification, the microparticulated form means a product obtained by disrupting or dispersing a killed lactic acid bacterium.

The disrupting or dispersing method of killed lactic acid bacteria is not particularly limited, and a dried product of a killed lactic acid bacterium may be dry pulverized and dispersed, or wet bacterial cells of a killed lactic acid bacterium may be wet disrupted and dispersed. To suppress damage on the surface-expressed target antigen, dry pulverization and dispersion is preferable.

The drying method of killed lactic acid bacteria is well known to those of ordinary skill in the art and is not particularly limited. For example, spray drying, freeze-dry and the like can be mentioned.

In the case of spray drying, for example, a killed lactic acid bacterium is dispersed in a solvent to give a bacterial cell dispersion. As a solvent, a known solvent used in the pertinent field may be used, and water is preferable. When desired, ethanol may be added. The above-mentioned bacterial cell solution may further contain additives generally used in the pertinent field, such as granulation agent, suspension, protector, excipient, binder, disintegrant, antistatic agent, buffering agent, dispersing agent, stabilizer, surfactant and the like, at a conventional addition rate. This bacterial cell dispersion is subjected to a drying operation by a spray dryer to give a dried product of a killed lactic acid bacterium. The dried product can be individual dried killed lactic acid bacteria, or an aggregate of dried killed lactic acid bacteria.

The dry pulverization and dispersion of killed lactic acid bacteria can be performed by a method known to those of ordinary skill in the art, such as bead mill, ball mill, jet mill and the like. Bead mill is a method of disrupting and dispersing a starting material by filling beads in a vessel, rotating the central rotation shaft to move the beads, feeding the starting material therein, and grinding same by the beads. Ball mill is a method of disrupting and dispersing a starting material by placing balls and the starting material in a pot, and rotating the pot to utilize drop impact of the balls. Jet mill is a method of disrupting and dispersing a starting material by pressurizing the starting material at a high pressure, discharging same at a high speed from fine nozzles to utilize impact between particles or against a hard member, shear force produced during passage through nozzles and counterflow, or impact force by jet cavitation. While a microparticulation method of a killed lactic acid bacterium is not particularly limited, to suppress damage on the surface-expressed target antigen, the bead mill is preferable. Microparticulation by a bead mill can be performed, for example, by a commercially available apparatus such as starmill (Ashizawa Finetech) and the like.

The oral preparation of the present invention can be produced by mixing a killed lactic acid bacterium expressing, on the surface, an antigen of a pathogen, or a microparticulated form thereof, which has a particle size of 2.68-30 μm and is the active ingredient, with a pharmaceutically acceptable carrier such as excipient, binder, disintegrant, lubricant and the like, and formulating the mixture into tablet (including sublingual tablet, oral disintegrant), capsule (including soft capsule, microcapsule, seamless capsule), powder, granule, pill, suspending agent, troche, syrup, emulsion and the like, according to a conventional means. These preparations may be controlled-release preparations such as immediate-release preparation, sustained-release preparation, enteric-coated drug and the like. The pharmaceutically acceptable carrier to be used is not particularly limited. Examples of the excipient include lactose, cornstarch, sucrose, glucose, mannitol, sorbitol, crystalline cellulose, silicon dioxide and the like. Examples of the binder include polyvinyl alcohol, polyvinyl ether, ethylcellulose, methylcellulose, gum arabic, tragacanth, gelatin, shellac, hydroxypropyl cellulose, hydroxypropyl methylcellulose, hydroxypropylstarch, polyvinylpyrrolidone and the like. Examples of the disintegrant include starch, agar, gelatin powder, crystalline cellulose, calcium carbonate, sodium hydrogen carbonate, calcium citrate, dextrin, pectin, carboxymethyl cellulose.calcium, low-substituted hydroxypropyl cellulose, croscarmellose sodium, partially α-nized starch and the like. Examples of the lubricant include magnesium stearate, talc, polyethylene glycol, silica, hydrogenated vegetable oil and the like.

The subject of administration of the oral preparation of the present invention is a mammal, and examples thereof include human, dog, cat, bovine, horse, swine and the like, with preference given to human.

When the oral preparation of the present invention is used for the prophylaxis of diseases (e.g., cervical cancer caused by HPV infection) with infection by a pathogen, the oral preparation of the present invention is administered to a mammal (e.g., human) having a risk of infection with the pathogen (e.g., HPV). When the oral preparation of the present invention is used for the treatment of diseases with infection by a pathogen (e.g., cervical cancer caused by HPV infection), the oral preparation of the present invention is administered to patients infected with the pathogen or patients infected with the pathogen and developed a disease caused thereby. Since the oral preparation of the present invention is superior in the effect of efficiently inducing the cellular immunity, the oral preparation of the present invention is administered to patients who were infected with a particular pathogen (e.g., HPV) but have not developed a disease or symptom (e.g., cervical cancer precancerous lesion and cervical cancer) caused by infection with the pathogen, whereby the onset of a disease caused by the infection can be effectively prevented. Alternatively, the oral preparation of the present invention is administered to patients in initial stages (e.g., precancerous lesion of cervical cancer) of a disease caused by infection with a particular pathogen (e.g., HPV), whereby progression of the disease caused by the infection (e.g., shift to cervical cancer) can be effectively prevented. In the present invention, prevention of the condition wherein infection with a particular pathogens has occurred but a disease caused by the infection has not been developed from progressing to the onset of diseases and symptoms caused by the infection, and prevention of the progress of the initial stages of a disease caused by infection with a particular pathogen to subsequent stages are encompassed in the "treatment of a disease with infection by a pathogen". In addition, administration of the oral preparation of the present invention to a target mammal (e.g., human) can induce cellular immunity to the target antigen in the target mammal.

In one embodiment, the oral preparation of the present invention provides an oral preparation for the prophylaxis or treatment of HPV infectious diseases, which contains a killed lactic acid bacterium expressing E7 of HPV on the surface or a microparticulated form thereof. By administering the oral preparation of the present embodiment to a patient who was infected with HPV but has not developed cervical cancer precancerous lesion or cervical cancer caused by HPV infection, the onset of cervical cancer precancerous lesion and cervical cancer can be efficiently prevented. In addition, by administering the oral preparation of the present embodiment to a patient with cervical cancer precancerous lesion caused by HPV infection, shift from cervical cancer precancerous lesion to cervical cancer can be effectively prevented.

The dose of the oral preparation of the present invention can be appropriately determined according to the kind of target antigen, the kind of target pathogen, target disease, age and conditions of patients and the like. For example, when the oral preparation of the present invention containing a killed lactic acid bacterium expressing human papilloma virus antigen (e.g., E7) on the surface or a microparticulated form thereof as an active ingredient is administered for the treatment of a human papilloma virus infectious disease (i.e., cervical cancer), a dose per administration for one person is, for example, 10 mg-10 g as a dry weight of the killed lactic acid bacterium or a microparticulated form thereof. The dose is not limited to this range as long as human papilloma virus infectious diseases can be treated. An oral preparation containing a killed lactic acid bacterium (particle size about 174.2 μm) as an active ingredient affords a superior therapeutic effect for cervical cancer at a dose of 1 g per administration. Since the oral preparation of the present invention shows improved cellular immunity induction potency by setting the particle size of a killed lactic acid bacterium or a microparticulated form thereof to 2.68-30 μm, an equivalent therapeutic effect for cervical cancer is expected at a dose less than 1 g (e.g., ½-1/10 dose thereof).

To enhance the cellular immunity to the target antigen by repetitive immunization, the oral preparation of the present invention is preferably administered plural times over 1-4 weeks at a frequency of once per 1-3 days.

EXAMPLES

While the present invention is explained in more detail in the following by referring to the Examples, they are mere examples and do not limit the scope of the present invention in any way.

Reference Example 1

The production method of the killed lactic acid bacterium preparation used in the following Examples is as described below. That is, according to the method described in YAKUGAKU ZASSHI 129(11) 1327-1332 (2009), lactic acid bacterium (*Lactobacillus casei*) expressing E7 of HPV on the surface was prepared. The lactic acid bacterium was killed using the method described in JP-B-4902845 to give a killed lactic acid bacterium expressing E7 on the surface. The killed lactic acid bacterium was freeze-dried. The particle size of the freeze-dried killed lactic acid bacterium was measured by SEM to find that the particle size was 30 µm. To the freeze-dried killed lactic acid bacterium were added hypromellose and magnesium stearate as granulating agents, and the mixture was granulated to give granules having a median particle size of 174.2 µm.

Example 1

Microparticulation of Lactic Acid Bacterium Vaccine—1

The current preparation is a granule having a median particle size of 174.2 µm. The conditions for microparticulation thereof were studied.

Using starmill of Ashizawa Finetech (generally called a beads mill), pulverization conditions were studied. The granule was sampled over time and the particle size was measured. As a result, particles with 14.4-2.5 µm median size were obtained, and finally, microparticles having a median particle size of 0.12 µm could be obtained (FIG. 1). The antigen (E7) protein amount measured by sandwich ELISA before and after microparticulation was 4.0 and 3.6 mg/g of powder, respectively, and damage on the antigen protein due to the microparticulation step was scarcely observed.

From the foregoing, a killed lactic acid bacterium expressing E7 on the surface was successfully microparticulated without decreasing the antigen protein.

The median particle size was measured by a laser diffraction scattering method using LA950V2 (manufactured by HORIBA) and ethanol as a dispersing medium.

Example 2

Microparticulation of Lactic Acid Bacterium Vaccine—2

For the microparticulation in Example 1, a granule with a particle size of 174.2 µm was used as a starting sample, which contained hypromellose and magnesium stearate as granulating agents. Thus, using an additive-free freeze-dried lactic acid bacterium as a starting sample, microparticulation by starmill was performed. The median particle size of the starting sample was 30 µm, which was pulverized to give fine particles of a killed lactic acid bacterium having various sizes of 9.17-0.49 µm (median size) (FIG. 2). The median size of the microparticulated form was measured by a laser diffraction scattering method in the same manner as in Example 1 by using LA920 (manufactured by HORIBA). The median size of the starting sample was measured based on SEM (scanning electron microscope) images.

Example 3

Study of M Cell Permeability

Figure 3:
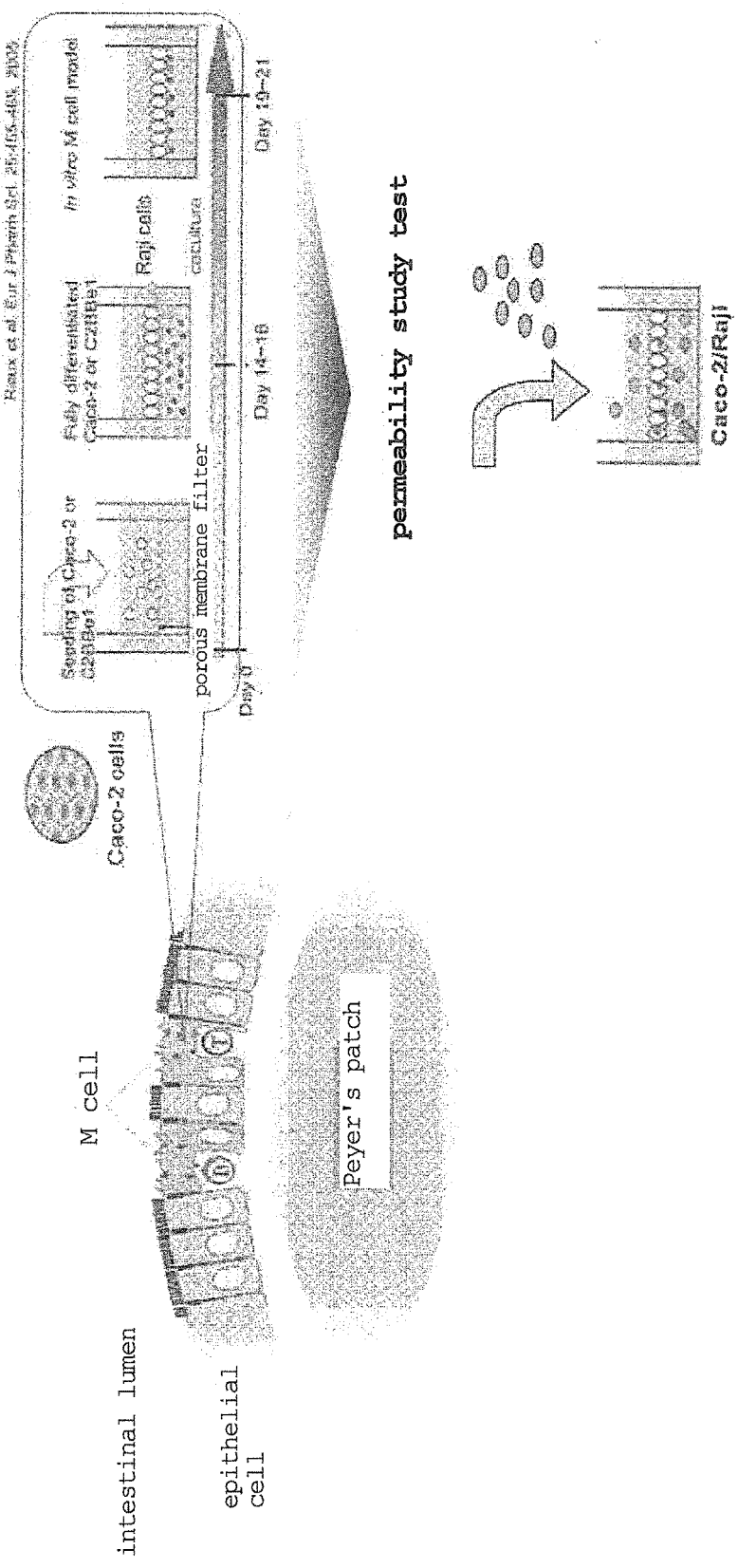
FIG. 3 shows a conceptual diagram of in vitro M cell model.

It is known that uptake from small intestine Peyer's patch M cells markedly increases when the particle size becomes small. For confirmation, a permeability test using an in vitro M cell model was performed according to Eur J Pharm Sci 25: 455-465, 2005 (FIG. 3).

Figure 4:
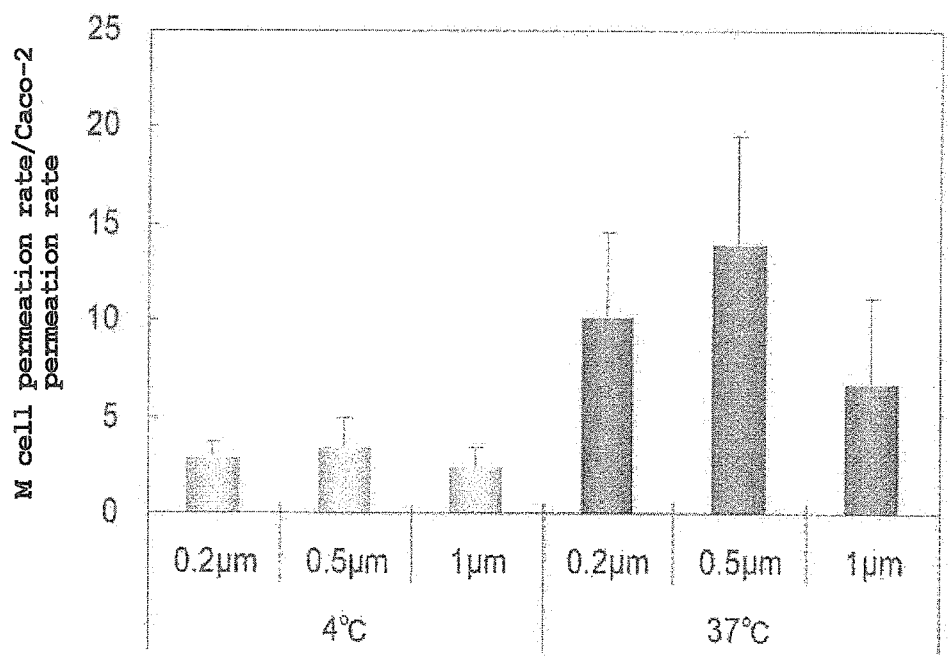
FIG. 4 shows the results of in vitro M cell permeability of microspheres having various particle sizes.

For confirmation of M cell model construction, and comparison of permeability by particle size, fluorescence labeled microsphere (particle size 0.2, 0.5, and, 1.0 µm) was used for investigation. Coculture of Caco-2 cell/Raji cell (M cell model) increased permeability of the microsphere as compared to Caco-2 cell single layer culture, and high permeability at 37° C. indicates uptake by transcytosis of M cell, whereby construction of M cell-like model was confirmed. As a result of comparison of permeability by particle size by using the model, a tendency toward high permeability was suggested at a particle size of less than 1 µm (FIG. 4).

Figure 5:
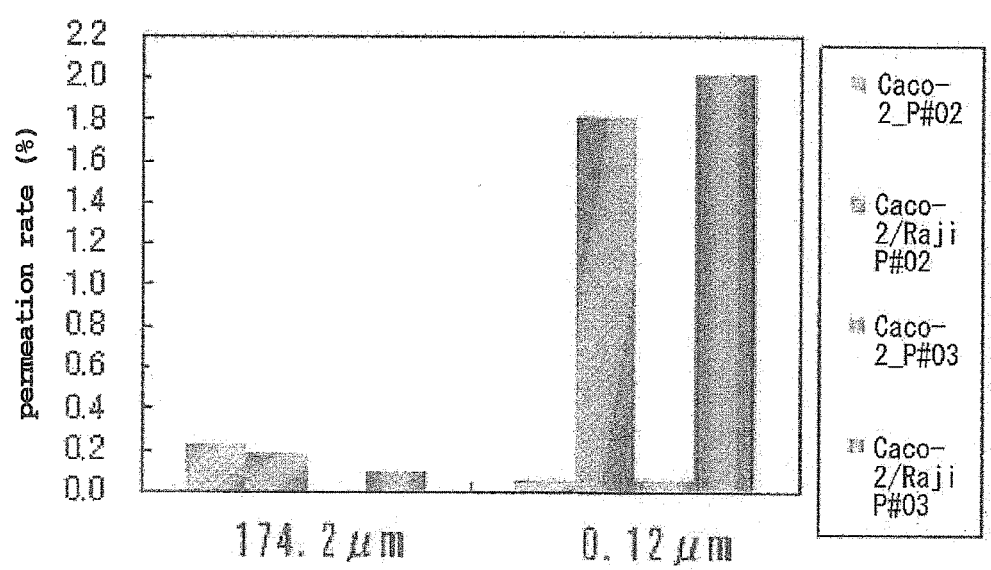
FIG. 5 shows the results of in vitro M cell permeability of a killed lactic acid bacterium or a microparticulated form thereof having various particle sizes. The bar indicating Caco-2 shows a test system (=mesentery model) wherein Caco-2 cells alone were subjected to single layer culture and the cells did not show M cell-like changes. The bar indicating Caco-2/Raji shows a test system (=M cell model) wherein Caco-2 cells and Raji cells were cocultured to afford M cell-like cells. P#02 and P#03 correspond to two independent tests.

By reference to the study results by the microsphere, a similar experiment was performed using a microparticulated lactic acid bacterium. First, in the study of permeability of a granule (median particle size 174.2 µm) and a sample (median particle size 0.12 µm) microparticulated from the granule, the permeability of a 0.12 µm microparticulated sample was confirmed to be significantly high (FIG. 5).

Then, the permeability of a freeze-dried sample (30 µm) free of a granule and samples obtained by microparticulation thereof (2.68 µm, 0.77 µm, 0.49 µm) was studied. As a result, large lactic acid bacterium particles of 174.2 µm, 30 µm showed low permeability of M cell model, and particles of 2.68 µm, 0.77 µm were confirmed to show high permeability due to the uptake by transcytosis of M cell. Furthermore, microparticulation to 0.49 µm resulted in remarkable promotion of permeability (FIG. 6).

Example 4

In Vivo Immunity Induction Potency Test

Figure 8:
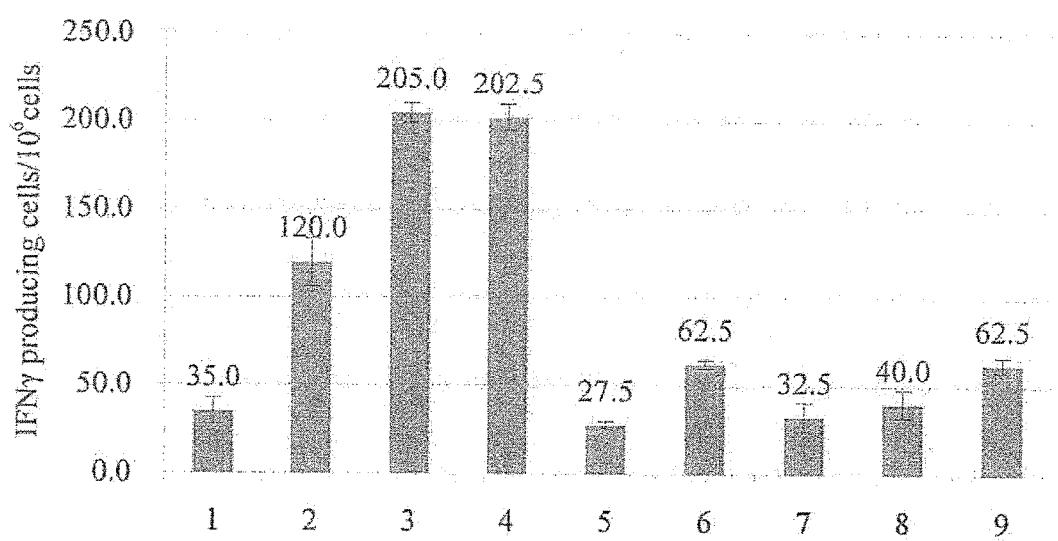
FIG. 8 shows comparison results of in vivo cellular immunity induction potency (IEL). The group constitution is the same as that in FIG. 7.

The influence of particle size of lactic acid bacterium vaccine and administration dosage on immunity induction potency were verified (FIG. 7). A killed lactic acid bacterium expressing E7 on the surface was orally administered to mouse on weeks 1, 2, 4, 8 each at 5 times/week. On week 9, the mouse was autopsied, IEL (intestinal epithelial lymphocyte) was separated from the small intestine, and splenocyte was separated from the spleen. The number of IFNγ-producing cells on stimulation with E7 was measured by ELISpot Assay (FIG. 8). As compared to the current preparation (median particle size 174.2 µm), the number of IFNγ-producing cells, which is an index of cellular immunity, was high in killed lactic acid bacterium (or a microparticulated form thereof) with a median particle size of 30 µm or 2.68 µm. On the other hand, microparticulated forms of a killed lactic acid bacterium with median particle size of 0.77 and 0.49 µm did not show an increase in the number of producing cells.

While it has been demonstrated that the uptake from M cell becomes high at a submicron level, sufficient induction of immunity was not confirmed in a lactic acid bacterium vaccine microparticulated to a submicron level in an in vivo immunity induction test.

INDUSTRIAL APPLICABILITY

According to the present invention, cellular immunity induction potency to a target antigen in oral administration can be improved by setting the particle size of a killed lactic acid bacterium expressing the target antigen on the surface or a microparticulated form thereof to fall within the range of 2.68-30 μm, and therefore, the effective dose of an oral vaccine containing, as an active ingredient, the killed lactic acid bacterium expressing the target antigen on the surface can be reduced.

This application is based on a patent application No. 2013-088800 filed in Japan (filing date: Apr. 19, 2013), the contents of which are incorporated in full herein.

The invention claimed is:

1. An oral preparation for the prophylaxis or treatment of a disease with infection by human papilloma virus, comprising a microparticle of a killed lactic acid bacterium expressing, on the surface, an E7 antigen of human papilloma virus, wherein the microparticle comprises a killed lactic acid bacterium, hypromellose and magnesium stearate, and the microparticle has an average particle size of 2.68-30 μm.

2. The oral preparation according to claim 1, wherein the killed lactic acid bacterium is a particle formed by subjecting a lactic acid bacterium to a heat treatment and freeze-drying the killed lactic acid bacterium.

3. The oral preparation according to claim 1, wherein the lactic acid bacterium is *Lactobacillus casei*.

4. The oral preparation according to claim 2, wherein the microparticle is formed by granulating the killed lactic acid bacterium particle with hypromellose and magnesium stearate to form a granule, and reducing the size of the granule with a bead mill.

5. The oral preparation according to claim 1 for the prophylaxis or treatment of the disease with infection by human papilloma virus by inducing cellular immunity to the E7 antigen of human papilloma virus.

6. An oral preparation for inducing cellular immunity to an E7 antigen of human papilloma virus, comprising a microparticle of a killed lactic acid bacterium expressing the E7 antigen of human papilloma virus on the surface, wherein the microparticle comprises a killed lactic acid bacterium, hypromellose and magnesium stearate, and the microparticle has an average particle size of 2.68-30 μm.

7. The oral preparation according to claim 6, wherein the killed lactic acid bacterium is a particle formed by subjecting a lactic acid bacterium to a heat treatment and freeze-drying the killed lactic acid bacterium.

8. The oral preparation according to claim 6, wherein the lactic acid bacterium is *Lactobacillus casei*.

9. The oral preparation according to claim 7, wherein the microparticle is formed by granulating the killed lactic acid bacterium particle with hypromellose and magnesium stearate to form a granule, and reducing the size of the granule with a bead mill.

10. A microparticle of a killed lactic acid bacterium expressing an E7 antigen of human papilloma virus on the surface, comprising a killed lactic acid bacterium, hypromellose and magnesium stearate, and the microparticle has an average particle size of 2.68-30 μm, for use in the prophylaxis or treatment of a disease with infection by a human papilloma virus by oral administration.

11. The microparticle of claim 10, wherein the killed lactic acid bacterium is a particle formed by subjecting a lactic acid bacterium to a heat treatment and freeze-drying the killed lactic acid bacterium.

12. The microparticle of claim 11, wherein the lactic acid bacterium is *Lactobacillus casei*.

13. The microparticle of claim 12, wherein the microparticle is formed by granulating the killed lactic acid bacterium particle with hypromellose and magnesium stearate to form a granule, and reducing the size of the granule with a bead mill.

14. The microparticle of claim 10, wherein the disease with infection by human papilloma virus is prevented or treated by inducing cellular immunity to the E7 antigen of human papilloma virus.

15. A method for the prophylaxis or treatment of a disease with infection by human papilloma virus, comprising orally administering an effective amount of a microparticle of claim 10 to a patient.

16. The method according to claim 15 for the prophylaxis or treatment of the disease with infection by human papilloma virus by inducing cellular immunity to the E7 antigen of the human papilloma virus.

\* \* \* \* \*